(12) United States Patent
Doshi et al.

(10) Patent No.: US 8,240,309 B2
(45) Date of Patent: Aug. 14, 2012

(54) ADJUSTABLE NASAL DEVICES

(75) Inventors: Rajiv Doshi, Stanford, CA (US); Bryan Loomas, Los Gatos, CA (US); Elliot Sather, San Francisco, CA (US); Jeffrey W. Servaites, San Francisco, CA (US); Sandrine Lebas, San Francisco, CA (US); Patrick A. Myall, San Francisco, CA (US); Lea Kobeli, San Francisco, CA (US)

(73) Assignee: Ventus Medical, Inc., San Jose, CA (US)

(*) Notice: Subject to any disclaimer, the term of this patent is extended or adjusted under 35 U.S.C. 154(b) by 889 days.

(21) Appl. No.: 11/941,915

(22) Filed: Nov. 16, 2007

(65) Prior Publication Data

US 2008/0178874 A1    Jul. 31, 2008

Related U.S. Application Data

(60) Provisional application No. 60/859,715, filed on Nov. 16, 2006.

(51) Int. Cl.
*A61M 15/08* (2006.01)

(52) U.S. Cl. ......... 128/207.18; 128/200.24; 128/206.21; 128/207.13

(58) Field of Classification Search ............. 128/200.24, 128/203.22, 206.11, 206.21, 207.13, 207.18; 606/199
See application file for complete search history.

(56) References Cited

U.S. PATENT DOCUMENTS

| | | | |
|---|---|---|---|
| 69,396 A * | 10/1867 | Curtis ................ 128/204.13 |
| 628,111 A | 7/1899 | McHatton | |
| 669,098 A | 3/1901 | Overshiner | |
| 675,275 A | 5/1901 | Gunning | |
| 718,785 A * | 1/1903 | McNary .............. 128/207.18 |
| 746,869 A | 12/1903 | Moulton | |
| 774,446 A | 11/1904 | Moulton | |
| 810,617 A | 1/1906 | Carence | |
| 1,819,884 A | 8/1931 | Fores | |
| 2,198,959 A | 4/1940 | Clarke | |

(Continued)

FOREIGN PATENT DOCUMENTS

EP    0434258 A2    6/1991

(Continued)

OTHER PUBLICATIONS

Hakel et al.; Nasal obturator for velopharyngeal dysfunction in dysarthria: technical report on a one-way valve; Journal of Medical Speech-Language Pathology; vol. 12; No. 4; pp. 155-159; 2004.

(Continued)

*Primary Examiner* — Justine Yu
*Assistant Examiner* — LaToya M. Louis
(74) *Attorney, Agent, or Firm* — Shay Glenn LLP

(57) ABSTRACT

Described herein are adjustable whole-nose nasal devices having a first passageway for communication with a first nasal passage and a second passageway for communication with a second nasal passage, an airflow resistor that inhibits expiration more than inspiration, and an adjustable connector. The adjustable connector may include one or more adjustable joints or regions that allow the whole-nose device to conform to the spacing between a subject's nostrils, and/or the orientation and angle of the subject's nostrils. Also described herein are whole-nose devices having a single airflow resistor communicating with both of a subject's nasal passages. Methods of treating a disorder using the whole-nose nasal devices are also described.

9 Claims, 12 Drawing Sheets

U.S. PATENT DOCUMENTS

| | | |
|---|---|---|
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,593,315 A | 4/1952 | Kraft |
| 2,672,138 A | 3/1954 | Carlock |
| 2,751,906 A | 6/1956 | Irvine |
| 2,777,442 A | 1/1957 | Zelano |
| 3,145,711 A | 8/1964 | Beber |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,616,802 A | 11/1971 | Marinaccio |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,094,316 A | 6/1978 | Nathanson |
| 4,143,872 A | 3/1979 | Havstad et al. |
| 4,212,296 A | 7/1980 | Schaar |
| 4,220,150 A * | 9/1980 | King ................... 128/206.11 |
| 4,221,217 A * | 9/1980 | Amezcua ............... 128/206.11 |
| 4,226,233 A | 10/1980 | Kritzer |
| 4,240,420 A | 12/1980 | Riaboy |
| 4,267,831 A | 5/1981 | Aguilar |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,601,465 A | 7/1986 | Roy |
| 4,640,277 A | 2/1987 | Meyer et al. |
| 4,651,873 A | 3/1987 | Stolcenberg et al. |
| 4,739,987 A | 4/1988 | Nicholson |
| 4,822,354 A | 4/1989 | Elosegui |
| 4,854,574 A | 8/1989 | Larson et al. |
| 4,860,766 A | 8/1989 | Sackner |
| 4,862,903 A | 9/1989 | Campbell |
| 4,908,028 A | 3/1990 | Colon et al. |
| 4,913,138 A | 4/1990 | Yoshida et al. |
| 4,919,138 A | 4/1990 | Nordenstroom |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,033,312 A | 7/1991 | Stupecky |
| 5,038,621 A | 8/1991 | Stupecky |
| 5,059,208 A | 10/1991 | Coe et al. |
| 5,074,293 A | 12/1991 | Lott et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,414,627 A | 5/1995 | Wada et al. |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,535,739 A | 7/1996 | Rapoport et al. |
| 5,562,641 A | 10/1996 | Flomenblit et al. |
| 5,568,808 A | 10/1996 | Rimkus |
| 5,607,469 A | 3/1997 | Frey |
| 5,649,533 A | 7/1997 | Oren |
| 5,665,104 A | 9/1997 | Lee |
| 5,727,546 A | 3/1998 | Clarke et al. |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,803,121 A | 9/1998 | Estes |
| 5,823,187 A | 10/1998 | Estes et al. |
| 5,865,170 A | 2/1999 | Moles |
| 5,876,434 A | 3/1999 | Flomenblit et al. |
| 5,890,998 A | 4/1999 | Hougen |
| 5,899,832 A | 5/1999 | Hougen |
| 5,910,071 A | 6/1999 | Hougen |
| 5,911,756 A | 6/1999 | Debry |
| 5,947,119 A | 9/1999 | Reznick |
| 5,954,766 A | 9/1999 | Zadno-Azizi et al. |
| 5,957,978 A | 9/1999 | Blom |
| 5,992,006 A | 11/1999 | Datsikas |
| 6,004,342 A | 12/1999 | Filis |
| 6,083,141 A | 7/2000 | Hougen |
| D430,667 S | 9/2000 | Rome |
| 6,119,690 A | 9/2000 | Pantaleo |
| 6,165,133 A | 12/2000 | Rapoport et al. |
| 6,177,482 B1 | 1/2001 | Cinelli et al. |
| 6,189,532 B1 | 2/2001 | Hely et al. |
| 6,213,955 B1 | 4/2001 | Karakasoglu et al. |
| 6,258,100 B1 | 7/2001 | Alferness et al. |
| 6,287,290 B1 | 9/2001 | Perkins et al. |
| 6,293,951 B1 | 9/2001 | Alferness et al. |
| 6,369,126 B1 | 4/2002 | Cinelli et al. |
| 6,398,775 B1 | 6/2002 | Perkins et al. |
| 6,439,233 B1 | 8/2002 | Geertsema |
| 6,484,725 B1 | 11/2002 | Chi |
| 6,500,095 B1 | 12/2002 | Hougen |
| 6,510,846 B1 | 1/2003 | O'Rourke |
| 6,527,761 B1 | 3/2003 | Soltesz et al. |
| 6,561,188 B1 | 5/2003 | Ellis |
| 6,562,057 B2 | 5/2003 | Santin |
| 6,568,387 B2 | 5/2003 | Davenport et al. |
| 6,573,421 B1 | 6/2003 | Lemaire |
| 6,581,598 B1 | 6/2003 | Foran et al. |
| 6,585,639 B1 | 7/2003 | Kotmel et al. |
| 6,592,594 B2 | 7/2003 | Rimbaugh et al. |
| 6,592,995 B2 | 7/2003 | Topolkaraev et al. |
| 6,595,215 B2 | 7/2003 | Wood |
| 6,609,516 B2 | 8/2003 | Hollander et al. |
| 6,626,172 B1 | 9/2003 | Karow et al. |
| 6,626,179 B1 | 9/2003 | Pedley |
| 6,631,721 B1 | 10/2003 | Salter et al. |
| 6,679,264 B1 | 1/2004 | Deem et al. |
| 6,694,979 B2 | 2/2004 | Deem et al. |
| 6,722,360 B2 | 4/2004 | Doshi |
| 6,726,598 B1 | 4/2004 | Jarvis et al. |
| 6,737,160 B1 | 5/2004 | Full et al. |
| 6,769,432 B1 | 8/2004 | Keifer |
| 6,776,162 B2 | 8/2004 | Wood |
| 6,811,538 B2 | 11/2004 | Westbrook et al. |
| 6,841,716 B1 | 1/2005 | Tsutsumi |
| 6,848,446 B2 | 2/2005 | Noble |
| 6,863,066 B2 | 3/2005 | Ogle |
| 6,866,652 B2 | 3/2005 | Bierman |
| 6,872,439 B2 | 3/2005 | Fearing et al. |
| 6,921,574 B2 | 7/2005 | Cinelli et al. |
| 6,997,177 B2 | 2/2006 | Wood |
| 7,011,723 B2 | 3/2006 | Full et al. |
| 7,047,969 B2 | 5/2006 | Noble |
| 7,156,098 B2 | 1/2007 | Dolezal et al. |
| 7,175,723 B2 | 2/2007 | Jones et al. |
| 7,178,524 B2 | 2/2007 | Noble |
| 7,201,169 B2 | 4/2007 | Wilkie et al. |
| D542,407 S | 5/2007 | Stallard et al. |

| | | |
|---|---|---|
| 7,263,996 B2 | 9/2007 | Yung Ho |
| D566,834 S | 4/2008 | Barton |
| 7,422,014 B1 | 9/2008 | Smith |
| 7,559,326 B2 | 7/2009 | Smith et al. |
| 7,640,934 B2 * | 1/2010 | Zollinger et al. .......... 128/207.18 |
| 7,880,051 B2 | 2/2011 | Madsen et al. |
| 2001/0051799 A1 | 12/2001 | Ingenito |
| 2001/0056274 A1 | 12/2001 | Perkins et al. |
| 2002/0062120 A1 | 5/2002 | Perkins et al. |
| 2002/0077593 A1 | 6/2002 | Perkins et al. |
| 2002/0112729 A1 | 8/2002 | DeVore et al. |
| 2002/0157673 A1 | 10/2002 | Kessler et al. |
| 2003/0024527 A1 | 2/2003 | Ginn |
| 2003/0050648 A1 | 3/2003 | Alferness et al. |
| 2003/0070682 A1 | 4/2003 | Wilson et al. |
| 2003/0106555 A1 | 6/2003 | Tovey |
| 2003/0106556 A1 | 6/2003 | Alperovich et al. |
| 2003/0140925 A1 | 7/2003 | Sapienza et al. |
| 2003/0154988 A1 | 8/2003 | DeVore et al. |
| 2003/0158515 A1 | 8/2003 | Gonzalez et al. |
| 2003/0195552 A1 | 10/2003 | Santin |
| 2003/0209247 A1 | 11/2003 | O'Rourke |
| 2004/0016432 A1 | 1/2004 | Genger et al. |
| 2004/0020492 A1 | 2/2004 | Dubrul et al. |
| 2004/0020493 A1 | 2/2004 | Wood |
| 2004/0055606 A1 | 3/2004 | Hendricksen et al. |
| 2004/0112379 A1 | 6/2004 | Djupesland |
| 2004/0123868 A1 | 7/2004 | Rutter |
| 2004/0194779 A1 | 10/2004 | Doshi |
| 2004/0254491 A1 | 12/2004 | Ricciardelli |
| 2004/0261791 A1 | 12/2004 | Horian |
| 2004/0261798 A1 | 12/2004 | Rimkus |
| 2005/0010125 A1 | 1/2005 | Joy et al. |
| 2005/0011524 A1 | 1/2005 | Thomlinson et al. |
| 2005/0033344 A1 | 2/2005 | Dillard et al. |
| 2005/0051170 A1 | 3/2005 | Koo |
| 2005/0066965 A1 | 3/2005 | Cronk et al. |
| 2005/0133039 A1 * | 6/2005 | Wood ........................ 128/207.18 |
| 2005/0205095 A1 * | 9/2005 | Dolezal et al. ............. 128/206.11 |
| 2005/0279351 A1 * | 12/2005 | Lewis et al. ............... 128/200.23 |
| 2005/0284479 A1 | 12/2005 | Schrader et al. |
| 2006/0000472 A1 | 1/2006 | Fenton |
| 2006/0016450 A1 * | 1/2006 | Pearson et al. ........... 128/206.11 |
| 2006/0085027 A1 | 4/2006 | Santin et al. |
| 2006/0144398 A1 | 7/2006 | Doshi et al. |
| 2006/0150978 A1 | 7/2006 | Doshi et al. |
| 2006/0150979 A1 | 7/2006 | Doshi et al. |
| 2006/0169285 A1 * | 8/2006 | Bovo ........................ 128/206.11 |
| 2006/0266361 A1 * | 11/2006 | Hernandez ............... 128/206.11 |
| 2006/0283461 A1 | 12/2006 | Lubke et al. |
| 2007/0016123 A1 | 1/2007 | Jensen |
| 2007/0051364 A1 | 3/2007 | Jacobson et al. |
| 2007/0095349 A1 | 5/2007 | Hansmann et al. |
| 2007/0175478 A1 | 8/2007 | Brunst |
| 2007/0227542 A1 | 10/2007 | Kashmakov et al. |
| 2007/0277832 A1 | 12/2007 | Doshi et al. |
| 2007/0283962 A1 | 12/2007 | Doshi et al. |
| 2007/0287976 A1 | 12/2007 | Sherrill |
| 2007/0295338 A1 | 12/2007 | Loomas et al. |
| 2008/0023007 A1 | 1/2008 | Dolezal et al. |
| 2008/0032119 A1 | 2/2008 | Feldhahn et al. |
| 2008/0041397 A1 | 2/2008 | Hirs |
| 2008/0053460 A1 | 3/2008 | Wilson |
| 2008/0087286 A1 | 4/2008 | Jones |
| 2008/0099021 A1 | 5/2008 | Moore |
| 2008/0142014 A1 | 6/2008 | Jiang |
| 2009/0145441 A1 | 6/2009 | Doshi et al. |
| 2009/0145788 A1 | 6/2009 | Doshi et al. |
| 2009/0188493 A1 | 7/2009 | Doshi et al. |
| 2009/0194100 A1 | 8/2009 | Minagi |
| 2009/0194109 A1 | 8/2009 | Doshi et al. |
| 2011/0067709 A1 | 3/2011 | Doshi et al. |
| 2011/0240032 A1 | 10/2011 | Doshi |
| 2011/0240038 A1 | 10/2011 | Doshi et al. |

FOREIGN PATENT DOCUMENTS

| | | |
|---|---|---|
| EP | 1157663 A1 | 11/2001 |
| EP | 1205203 A2 | 5/2002 |
| EP | 1481702 A2 | 12/2004 |
| GB | 2324729 A | 4/1998 |
| JP | 55-122742 U | 9/1980 |
| JP | 58-136345 A | 8/1983 |
| JP | 63-189257 U | 12/1988 |
| JP | 7-47126 | 2/1995 |
| JP | 3059270 U | 3/1999 |
| JP | 2001-299916 A | 10/2001 |
| JP | 2002-219174 A | 8/2002 |
| JP | 2002-345963 A | 12/2002 |
| JP | 2002-345966 | 12/2002 |
| JP | 05/40589 A | 2/2005 |
| JP | 2005-505355 | 2/2005 |
| JP | 2008-136496 | 6/2008 |
| JP | 2008-522763 | 7/2008 |
| RU | 2048820 C1 | 11/1995 |
| SU | 1586709 A1 | 8/1990 |
| WO | WO 90/12614 A1 | 11/1990 |
| WO | WO93/08777 A1 | 5/1993 |
| WO | WO 95/17220 A1 | 6/1995 |
| WO | WO 95/33520 A1 | 12/1995 |
| WO | WO 99/03395 A1 | 1/1999 |
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO2005/000805 A2 | 1/2005 |
| WO | WO2006/040585 A1 | 4/2006 |
| WO | WO 2006/063339 A2 | 6/2006 |
| WO | WO2007/023607 | 3/2007 |
| WO | WO 2007/129814 A1 | 11/2007 |
| WO | WO 2007/134458 A1 | 11/2007 |
| WO | WO 2007/146133 A2 | 12/2007 |

OTHER PUBLICATIONS

Doshi et al.; U.S. Appl. No. 12/711,782 entitled "Respiratory devices," filed Feb. 24, 2010.

Sather et al.; U.S. Appl. No. 12/044,868 entitled "Respiratory sensor adapters for nasal devices," filed Mar. 7, 2008.

Pierce et al.; U.S. Appl. No. 12/141,875 entitled "Adhesive nasal respiratory devices," filed Jun. 18, 2008.

Sather et al.; U.S. Appl. No. 12/405,837 entitled "Nasal devices with noise-reduction and methods of use," filed Mar. 17, 2009.

Ferdinand et al.; U.S. Appl. No. 12/485,750 entitled "Adjustable resistance nasal devices," filed Jun. 16, 2009.

Loomas et al.; U.S. Appl. No. 12/877,836 entitled "Nasal respiratory devices for positive end-expiratory pressure," filed Sep. 8, 2010.

Doshi et al.; U.S. Appl. No. 12/884,140 entitled "Sealing nasal devices for use while sleeping," filed Sep. 16, 2010.

Doshi et al.; U.S. Appl. No. 12/884,146 entitled "Nasal devices for use while sleeping," filed Sep. 16, 2010.

Doshi et al.; U.S. Appl. No. 12/884,151 entitled "Nasal devices with respiratory gas source," Sep. 16, 2010.

Doshi et al.; U.S. Appl. No. 12/885,359 entitled "Methods of treating a sleeping subject," filed Sep. 17, 2010.

Doshi et al.; U.S. Appl. No. 12/885,366 entitled "Methods of treating a disorder by inhibiting expiration," filed Sep. 17, 2010.

Doshi et al.; U.S. Appl. No. 12/885,370 entitled "Quiet nasal respiratory devices," filed Sep. 17, 2010.

Doshi et al; U.S. Appl. No. 11/811,339 entitled "Nasal devices," filed Jun. 7, 2007.

Doshi et al; U.S. Appl. No. 11/941,913 entitled "Nasal device applicators," filed Nov. 16, 2007.

Doshi, Rajiv; U.S. Appl. No. 12/014,060 entitled "Methods and devices for improving breathing in patients with pulmonary disease," filed Jan. 14, 2008.

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

http://chinookmed.com/index.cfm/fa/product.display&Product_ID=275.

Dillard, D. et al., Evaluation of a novel intra-bronchial valve to produce lung volume reduction, World Congress of Bronchology, Jun. 2002 (figs. 1-4 available upon request).

Sather et al.; U.S. Appl. No. 12/941,734 entitled "Nasal devices having a safe failure mode and remotely activatable," filed Nov. 8, 2010.

Favet et al.; U.S. Appl. No. 13/035,524 entitled "Nasal devices including layered nasal devices and delayed resistance adapters for use with nasal devices," filed Feb. 25, 2011.

Lai et al.; U.S. Appl. No. 13/062,888 entitled "Nasal devices, systems and methods," filed Mar. 8, 2011.

Doshi et al.; U.S. Appl. No. 13/212,948 entitled "Packaging and dispensing nasal devices," filed Aug. 18, 2011.

Sather et al.; U.S. Appl. No. 13/117,933 entitled "Layered nasal respiratory devices," filed May 27, 2011.

Pierce et al.; U.S. Appl. No. 13/299,181 entitled "Adhesive nasal respiratory devices" filed Nov. 17, 2011.

* cited by examiner

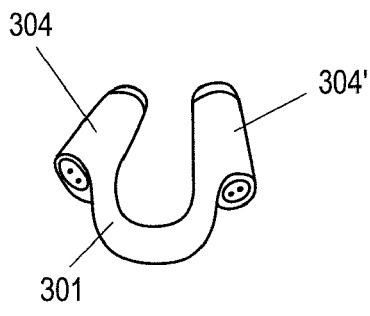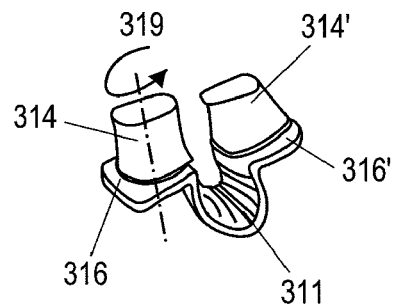
FIG. 3A  FIG. 3B
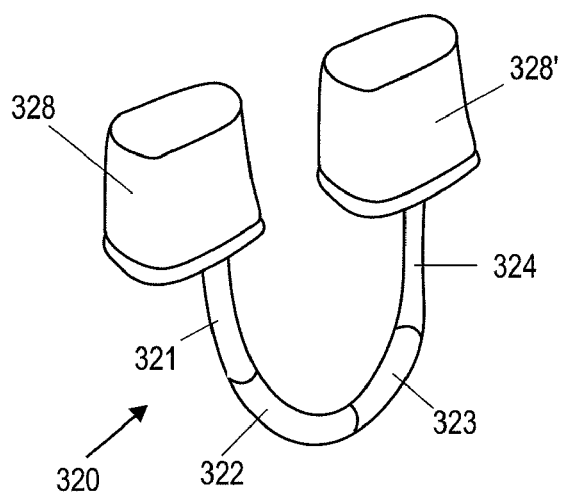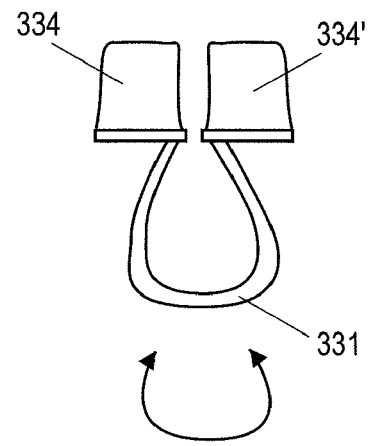
FIG. 3C  FIG. 3D

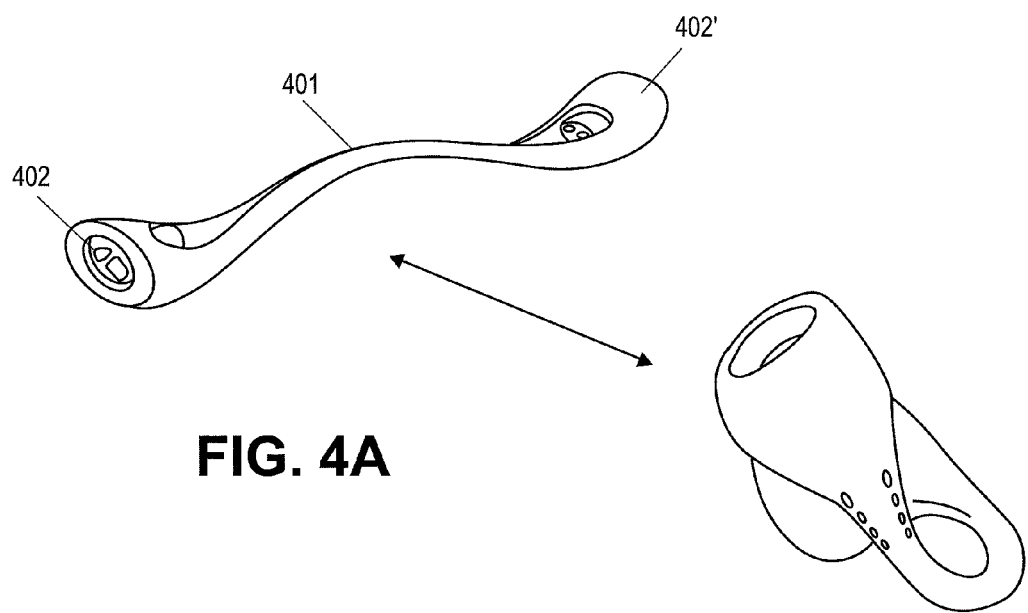
FIG. 4A
FIG. 4B
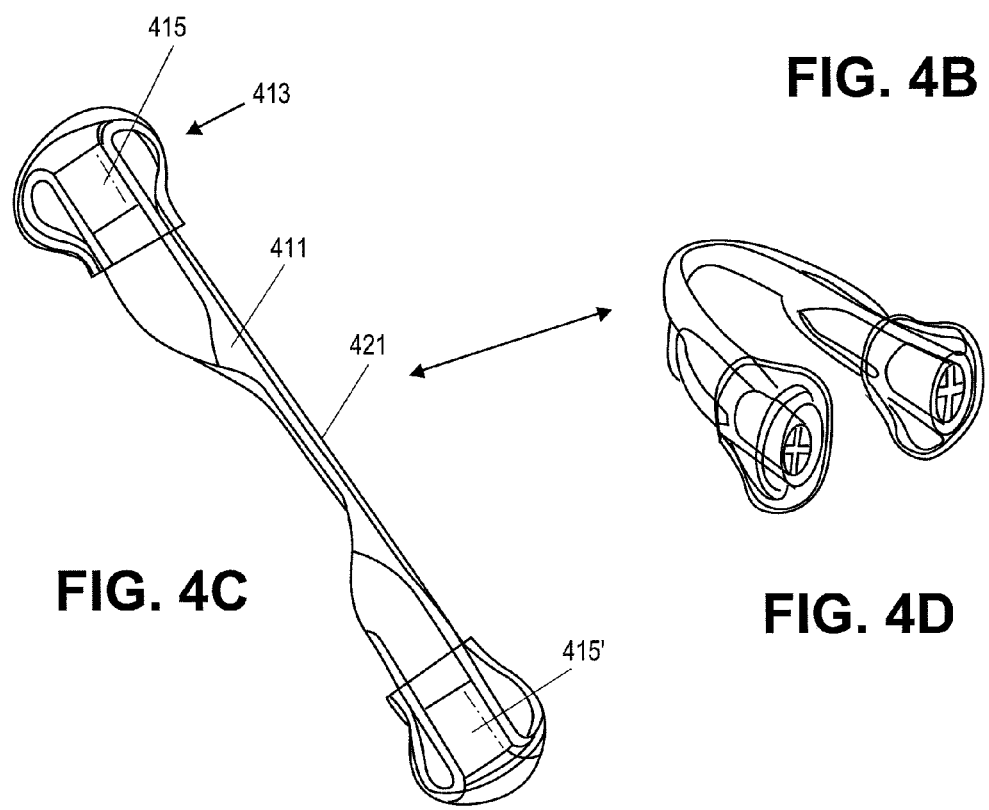
FIG. 4C
FIG. 4D

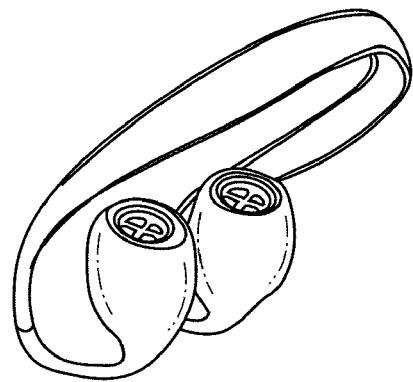
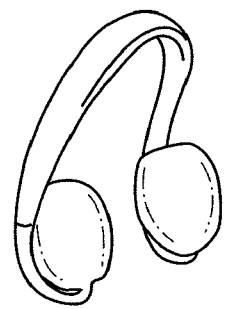
FIG. 11A  FIG. 11B
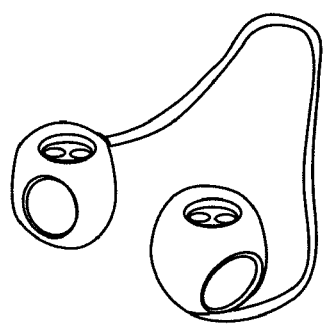
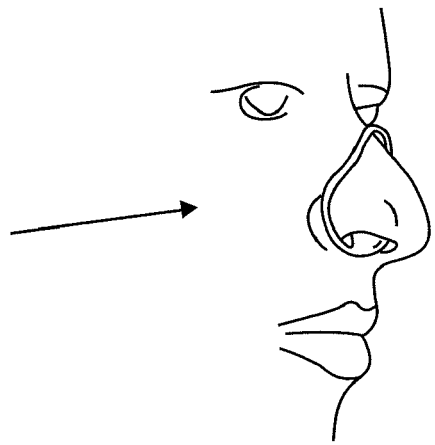
FIG. 11C  FIG. 11D
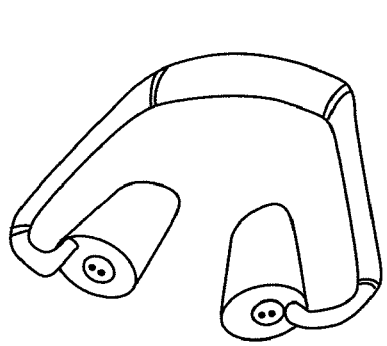
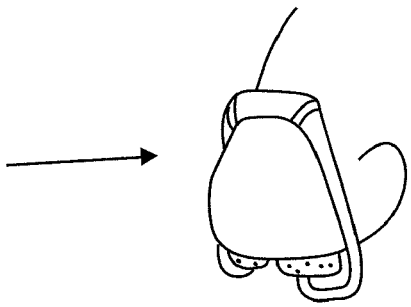
FIG. 11E  FIG. 11F

ADJUSTABLE NASAL DEVICES

CROSS-REFERENCE TO RELATED APPLICATIONS

This application claims the benefit of U.S. Provisional Patent Application 60/859,715 (titled "Nasal Devices"), filed Nov. 16, 2006. This provisional patent application is herein incorporated by reference in its entirety.

BACKGROUND OF THE INVENTION

The devices, methods, and kits described herein relate generally to applicators for nasal devices. These nasal devices may be therapeutically used to treat medical disorders, particularly in the fields of cardiovascular medicine, sleep medicine, pulmonology, gastroenterology, and internal medicine.

Nasal respiratory devices have been well-described in the following US patent applications, each of which is incorporated herein in its entirety: U.S. patent application Ser. No. 11/298,640, titled "NASAL RESPIRATORY DEVICES" (filed Dec. 8, 2005); U.S. patent application Ser. No. 11/298,339, titled "RESPIRATORY DEVICES" (filed Dec. 8, 2005); U.S. patent application Ser. No. 11/298,362, titled "METHODS OF TREATING RESPIRATORY DISORDERS" (filed Dec. 8, 2005); U.S. patent application Ser. No. 11/805,496, titled "NASAL RESPIRATORY DEVICES" (filed May 22, 2007); U.S. patent application Ser. No. 11/811,339, titled "NASAL DEVICES" (field Jun. 7, 2007); and U.S. patent application Ser. No. 11/759,916 (field Jun. 7, 2007).

These patent applications describe nasal respiratory devices, including devices configured to be applied in, over, or across a subject's nose to treat a variety of medical diseases or conditions. Examples of medical conditions that may be treated include but are not limited to snoring, sleep apnea (obstructive, central and mixed), Cheyne Stokes breathing, UARS, COPD, hypertension, asthma, GERD, heart failure, and other respiratory and sleep conditions. Nasal devices of particular interest are those that inhibit expiration more than inspiration. These devices may be placed in communication with a subject's nasal passage(s) without affecting respiration through the subject's mouth. One variation of these nasal devices are nasal respiratory devices configured to induce positive end-expiratory pressure ("PEEP") or expiratory positive airway pressure ("EPAP"), and are adapted to be removably secured in communication with a nasal cavity.

Exemplary nasal devices are described herein, and may include one or more airflow resistors that inhibit expiration more than inhalation. These devices may include a passageway with an opening at a proximal end, and an opening at a distal end, where the airflow resistor is in communication with the passageway. These devices typically also include a holdfast that is configured to removably secure the respiratory device within (or over, or around) the nasal passage or cavity.

Although single-nostril nasal devices have previously been described, "whole nose" nasal devices that integrate the function of two single-nostril nasal devices have not been developed in any detail. In particular, it has been challenging to develop whole-nose nasal devices that are capable of handling variations in the different nostril spacings, sizes and morphologies between subjects, as well as changes in shape and fit for a single subject during the period a subject is wearing a whole-nose device. Preparing low-cost and effective whole-nose devices that are comfortable and easy to use has likewise proven to be a challenge. Described herein are whole-nose devices that may address many of the problems identified above.

SUMMARY OF THE INVENTION

Described herein are nasal devices (also referred to as nasal respiratory devices) that may adjustably fit to communicate with both of a subject's nasal passages and provide a greater resistance to expiration through the nasal passages than to inhalation through the nasal passages. In particular, nasal devices including an adjustable connector that can be adjusted to comfortably fit the subject's nose while keeping one or more passive airflow resistor(s) of the nasal device in communication with both of the subject's nasal passages are described. Other nasal devices described herein include whole-nose nasal devices configured to secure a single airflow resistor in communication with both of a subject's nostrils (or nasal passageways) without inhibiting respiration through the subject's mouth. Methods of using these nasal devices are also described. In general, a whole-nose nasal device is a nasal device that is configured to communicate with both of a subject's nasal passages (e.g., both nostrils).

Described herein are nasal devices adapted to be secured in communication with a subject's nasal passage. These nasal devices include: a first passageway through a first body, wherein the first passageway is configured to fluidly connect with a subject's first nasal passage; a second passageway through a second body, wherein the second passageway is configured to fluidly connect to a subject' second nasal passage; a passive airflow resistor in communication with at least the first passageway, wherein the airflow resistor is configured to increase the resistance to exhalation more than inhalation; a holdfast configured to secure the respiratory device in communication with the subject's nasal passage; and an adjustable connector connecting the first body and the second body, wherein the connector is configured to adjust and hold the connector in a plurality of configurations.

As used herein, unless the context specifies otherwise, an airflow resistor is a passive airflow resistor. A passive airflow resistor is an airflow resistor that does not apply additional airflow (e.g., by blowing or sucking air). In general, a passive airflow resistor applies a greater resistance to expiration than to inhalation by reducing orifice size through which airflow through the device passes. For example, a passive airflow resistor may be a flap valve, a ball valve, etc.

The adjustable connector may be adjustable at the time of applying the nasal device to subject's nose, or it may be adjusted multiple times, including during operation of the nasal device (e.g., when the device is being worn). For example, a nasal device may be adjusted and positioned on the subject so that the first and second passageways are in communication with the subject's left and right nasal passages (respectively). Once positioned, the device may be locked or secured into this position by locking the adjustable connector. In some variations, the adjustable connector is also flexible, even after being adjusted to a set position. For example, the connector may be configured to flex and permit minor changes in the fit of the device to accommodate for movements (e.g., the relative positions of the subject's nasal passages as the subject moves), during talking, breathing, sleeping, etc. Examples of flexible connectors include a bendable wire, a spring, an accordion tube, etc.

A nasal device may include a single airflow resistor in communication with both nasal passages, or it may include a separate airflow resistor configured to communicate with each nasal passage separately. For example, the same airflow resistor may be in communication with the second passageway that is in communication with the first passageway. In another variation, a second airflow resistor is in communication with the second passageway, separate from the first airflow resistor in communication with the first passageway. In any of the examples, the airflow resistor provides a greater resistance to exhalation than to inhalation when the devices including them are worn by the subject.

A connector may have any appropriate configuration. For example, a connector may pass over the subject's nose (e.g., an over-the-nose connector), or it may pass under the subject's nose. In some variations, the connector does not cross the subject's nose at all, but passes around the back of the subject.

The connector (and particularly flexible connectors) may act as the holdfast. For example, the holdfast may be part of the connector. In some variations, the connector secures the device to the subject's nose (acting as a holdfast) by grasping at least a portion of the subject's nose.

An adjustable connector may include one or more movable joints, including hinge joints, ball joints, and flexible joints. For example, the connector may include a first mount for securing the first body, and a second mount for securing the second body. In some variations, the connector includes only a single mount connecting the first and second bodies. A mount may include a joint, such as a flexible joint, a ball joint, a hinge joint, an articulated (segmented) joint, or the like. In general the joint is movable. In some variations, the joint may be locked or tightened, so that is becomes less movable.

Also described herein are whole-nose nasal devices comprising a first single-nostril nasal device having a passageway and a first airflow resistor in communication with the passageway (wherein the first airflow resistor is configured to inhibit expiration more than inspiration), a second single-nostril nasal device having a passageway and a second airflow resistor in communication with the passageway (wherein the second airflow resistor is configured to inhibit expiration more than inspiration), and an adjustable connector connecting the first single-nostril nasal device and the second single-nostril nasal device, wherein the connector is configured to adjust and hold the connector in a plurality of configurations. The adjustable connector may include a hinge joint, a ball joint, or a flexible joint (or a plurality of such joints).

Also described herein are whole-nose nasal devices that include a passageway configured to communicate with both of a subject's nasal passages so that nasal breathing, but not oral breathing, will occur through the passageway, and an airflow resistor in communication with the passageway. The airflow resistor is configured to inhibit expiration more than inspiration. In some variations this device also includes a holdfast configured to secure the device to the subject's nose so that the passageway is in communication with both of the subject's nasal passages. The holdfast may be an adhesive holdfast that includes at least one adhesive surface for securing the device to the subject's nose. In some variations, this adhesive holdfast may releasably seal the device in communication with the subject's nasal passages.

Also described herein are methods of treating a disorder using an adjustable nasal device, particularly a nasal device including a first passageway configured to communicate with a subject's right nasal passage and a second passageway configured to communicate with the subject's left nasal passage, an airflow resistor in communication with at least the first passageway that inhibits expiration more than it inhibits inhalation, and an adjustable connector. The method may include the steps of adjusting the adjustable connector of the nasal device so that the first passageway is in communication with the subject's right nasal passage and the second passageway is in communication with the subject's left nasal passage, and securing the nasal device to the subject.

The disorder to be treated by any of the methods of treatment described herein may be a respiratory disorder, a sleep disorder, a gastroenterologic disorder, and/or a cardiovascular disorder. For example, snoring may be treated by these devices. In some variations, sleep apnea may be treated by the methods described herein.

Also described herein are methods of treating a disorder using a whole-nose nasal device, wherein the whole-nose nasal device includes a body having a first passageway and a second passageway, and an airflow resistor in fluid communication with the first and second passageways (wherein the airflow resistor is configured to inhibit expiration more than inspiration). These methods may include the steps of securing the first passageway of the nasal device over the subject's right nasal passage and the second passageway of the nasal device over the subject's left nasal passage, and allowing the subject to breathe through the nasal device, thereby inhibiting nasal expiration more than nasal inhalation.

INCORPORATION BY REFERENCE

All publications and patent applications mentioned in this specification are herein incorporated by reference in their entirety to the same extent as if each individual publication or patent application was specifically and individually indicated to be incorporated by reference.

BRIEF DESCRIPTION OF THE DRAWINGS

FIGS. 3A-3D are other variations of whole-nose nasal devices.

FIGS. 4A and 4B show a whole-nose nasal device in a first and second configuration, respectively.

FIGS. 4C and 4D show another variation of a whole-nose nasal device in a first and second configuration, respectively.

FIGS. 11A-11C are over-the-nose whole-nose nasal devices.

FIG. 11D illustrates a subject wearing the device of FIG. 11C.

FIG. 11E is another variation of a whole-nose nasal device configured to fit over a subject's nose.

FIG. 11F illustrates the device of FIG. 11E on a subject's nose.

DETAILED DESCRIPTION OF THE INVENTION

Figure 1A:
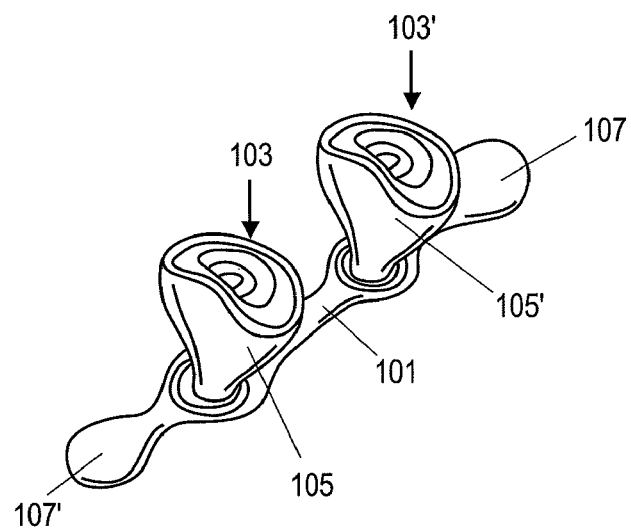
FIGS. 1A and 1B are different variations of whole-nose nasal devices.

Described here are whole-nose nasal respiratory devices and methods for their use, and particularly whole-nose nasal devices configured to limit nasal expiration more than nasal inhalation through the entire nose that include an adjustable connector. The nasal devices described herein are configured to fit in, over and/or around both nostrils (nasal passages). These nasal respiratory devices may be referred to as nasal devices, "whole-nose nasal devices", nasal respiratory devices, or simply as "devices." The devices and methods described herein may be useful to treat a variety of medical disease states, and may also be useful for non-therapeutic purposes. The devices and methods described herein are not limited to the particular embodiments described. Variations of the particular embodiments described may be made and still fall within the scope of the disclosure. It is also to be understood that the examples and particular embodiments described are not intended to be limiting.

As used in this specification, the singular forms "a," "an," and "the" include plural reference unless the context clearly dictates otherwise. The following descriptions including various design parameters or goals, and methods and devices which fit the design parameters or goals. It should be understood that the devices and methods described herein (and recited by any claims) are not limited to any particular theory of operation.

Many of the devices described herein include: one or more passageways through which air may pass to enter or exit a respiratory orifice; a holdfast for securing the device to, over, and/or within a subject's respiratory orifice; and one or more airflow resistor (or valve) for regulating the passage of air through the passageway(s). As will be apparent from the figures, many of these devices and methods for using them are easy to use, and may be removable and insertable by a subject (without special tools). The nasal devices may be disposable or durable (e.g., reusable) in whole or in part.

The airflow resistors described herein are passive airflow resistors, and not active airflow resistors. An active airflow resistor applies a pressure (which may be constant or variable) by providing a flow of continuous (e.g., "positive") air pressure. A passive airflow resistor does exert resistance by applying differential air pressure (blowing or sucking). Instead, the passive airflow resistors typically reduce the size of the passageway or aperture through which airflow passes. Thus, a passive airflow resistor may include a flap valve, a ball valve, or the like.

The nasal devices described herein may include a holdfast. A holdfast may facilitate the positioning and securing of the device in a desired location, such as over or within (e.g., substantially within) the nostrils. In particular, the holdfast may allow the device to be anchored, positioned, and/or stabilized so that the passageway (or passageways) of the device are in communication with the nostrils of the subject wearing the device.

The phrase "in communication with" may mean "in fluid communication with". In particular, the passageway or passageways of the devices described herein may be in communication with one or both of a subject's nostrils. This means that respiratory airflow through the nostrils will pass in whole or in part through the passageway(s) that are in communication with the nostrils. Typically the passageways of the device are in communication with the nostrils so that only nasal respiratory airflow, but not oral respiratory airflow, passes through them.

The devices described herein may also include a handle that may help insert and/or position the device. In some variations, a holdfast may be configured as a handle. In some variations, the connector (e.g., adjustable connector) is configured as a handle. In other variations, a separate (or separable) handle may be used.

In some variations, two single-nostril nasal devices are connected by a connector (which may also be referred to as a "bridge"). Adjustable connectors (described in more detail below) are of particular interest. A connector may be integral to the nasal devices (e.g., formed from the same part as one or more components of the single-nostril nasal device), or it may be formed separately. For example, the connector may be formed from the holdfast region of each device to which it connects. A connector may also act to support or secure two single nostril nasal devices to form a whole-nose nasal device. For example, a connector may act as a frame onto which nasal devices are attached (including releasably attached). A connector may also include or be configured as a handle (as mentioned above) for grasping and/or inserting or positioning the device(s). A connector may be semi-rigid or rigid, and adjustable or flexible so that it allows the device to be fit to a subject's nose or nasal passages. A connector may be customized or customizable to a particular subject. Furthermore, a connector may be durable (reusable over many weeks, months or even years), partially reusable (e.g., over days or weeks), or disposable (single-use or used for a few days). Thus, different ("fresh") nasal devices may be used with an existing bridge or connector to form a nasal device.

Examples of whole-nose nasal devices that do not include adjustable connectors are shown in FIGS. 1A-2D. Although the connectors in FIGS. 1A-2D are not adjustable connectors, they are flexible. For example, in FIG. 1A, the nasal device is a whole-nose nasal device having two passageways 103, 103' that are each in communication with an airflow resistor (not shown) and each is configured to be held in fluid communication with a subject's nostril. The passages are formed through a body region 105, 105' and the body region is surrounded by a holdfast material that can be configured (e.g., as a foam) to secure each body region within the subject's nose. The connector 101 is a band of material (e.g., an adhesive material) that is connected to each of the body regions 105, 105' having a passageway. In this variation, the connector 101 is also configured as a holdfast, and may include an adhesive surface so that the connector 101 can be secured to the subject's face. An additional holdfast region 107, 107' is shown projecting from the ends of the whole-nose device as two tab regions that can also be adhesively secured to the subject. These tab regions may act as a handle that help apply the device.

Figure 1B:
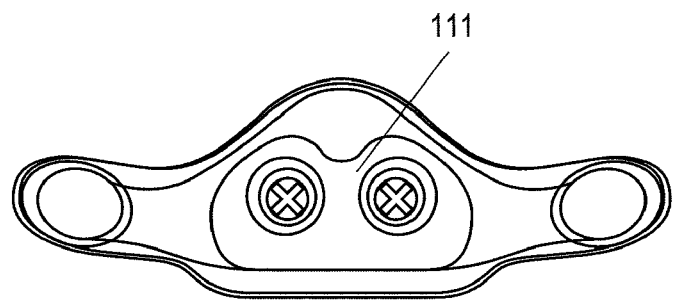
Figure 1C:
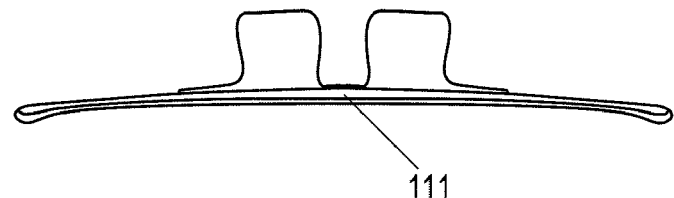
FIG. 1C is a side view of the whole-nose nasal device of FIG. 1B.
Figure 2D:
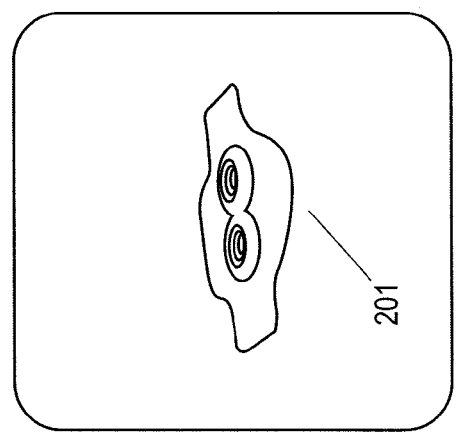
FIGS. 2A-2D illustrate one method of applying a whole-nose nasal device.
Figure 2C:
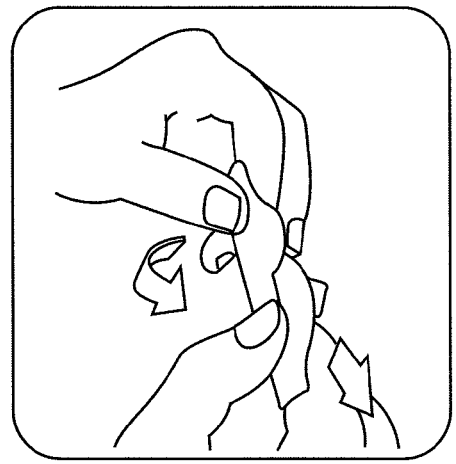
Figure 2B:
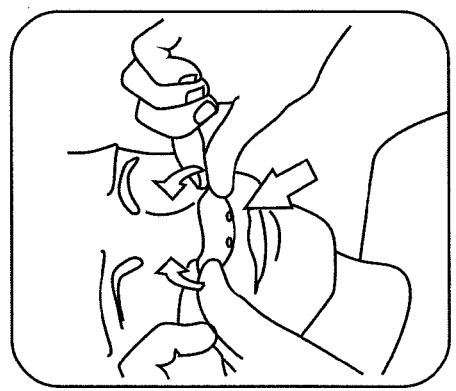

FIG. 1B is a top view of another variation of a whole-nose nasal device having two passageways configured to communicate with a subject's nostrils, similar to the variation shown in FIG. 1A. FIG. 1C shows a side view of the device of FIG. 1B. In FIG. 1B, the connector 111 is a fixed distance between the bodies forming the passageways. FIGS. 2A-2D illustrate a method of applying a similar whole-nose nasal device, which is an adhesive whole-nose nasal device. To apply the device, the adhesive layer is exposed by removing a protective backing, as shown in FIG. 2B, and the device can be manually applied over the subject's nose, as shown in FIGS. 2C and 2D.

As mentioned, the holdfast region of the nasal device may include an adhesive material to help secure the nasal device over, around, or within a nasal passage. In some variations, the holdfast region limits nasal respiratory airflow to the nasal device. For example, the holdfast may form a seal. The holdfast may be substantially flat and bandage-like, having at least one adhesive surface for contacting the subject's nose.

Figure 2A:
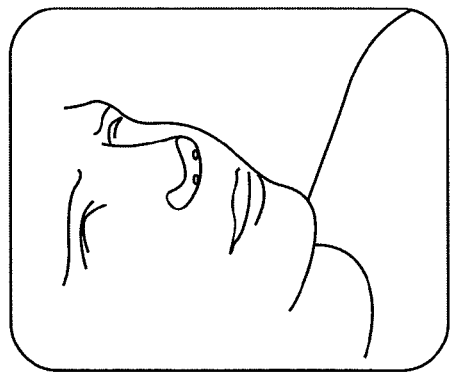

The nasal device shown in FIG. 2A includes a holdfast region that secures the device against each nostril. As mentioned previously, the holdfast may comprise any appropriate material, including a porous material and/or an elastic material. Further, the adhesive may be any appropriate biocompatible adhesive. In some variations, the holdfast is sufficiently breathable so that fluid (e.g., sweat, skin oils, etc.) may pass through it.

Connectors

In general, a whole-nose nasal device may include a connector to connect the two passageways that are configured to communicate with the nostrils. Typically each passageway is formed through a body region of the device. In some variations, these body regions are formed from single-nostril nasal devices that could be used independently, without a connector, one in each of a subject's nostrils. A connector is preferably an adjustable connector, described in detail below. A connector may be formed of any appropriate material, and may be a discrete (e.g., separable) element of the whole-nose nasal device, or it may be formed as an integral part of the nasal device. For example, a connector may be formed as part of a region of a nasal device, such as the holdfast region. Thus, a connector may include a holdfast, and two single-nostril devices may share the same holdfast.

A connector, including an adjustable connector, may be flexible, semi-rigid, or rigid. Flexible connectors may 'flex' slightly as the subject wearing the device moves, enhancing comfort and prevent the device from disengaging. Semi-rigid and rigid connectors may help provide support and durability. Regions of the connector may be more or less flexible or more or less rigid.

A connector may be reusable. For example, a connector may be configured to secure to two single-nostril nasal devices by securing to a region of the device forming a passageway (e.g., a body region). Thus, a connector may include a mount for linking the connector to each single-nostril device. The mount typically secures each passageway (e.g., each single-nostril nasal device) to the connector. A mount may be permanent (e.g., a connector may be permanently affixed to the single-nostril device), or it may be releasable. For example, a mount may be a snap-fit, a clip, or other linking structure. Thus, the same connector may be re-used with new (e.g., "fresh") single-nostril nasal devices.

In addition to bridging the two passageways of the whole-nose device, a connector may also act as a handle that can assist in applying the nasal device. Thus, a connector may include one or more gasping surfaces that a subject may hold and position or adjust the device. The connector may also include a holdfast or a portion of the holdfast for securing the whole-nose device to the subject.

A nasal device connector may be an adjustable connector. An adjustable connector typically connects two passageways each configured to communicate with one of a subject's nostrils, so that the spacing between the passageways may be adjusted to the nostril spacing of the subject. Adjustable connectors may allow adjustment in multiple axes. The first axis that may be adjusted is the separation between the nostrils, referred to as the nostril spacing axis. Thus, a whole-nose device may be adjusted so that the separation between the two passageways (or the body regions forming the passageways) are movable to match the distance between the nostrils. Another axis that may be adjusted by an adjustable connector is the nostril angular axis, which refers to the angle formed between the long axis of the nasal passageway (e.g., with the medial axis of the body). Thus, an adjustable connector may allow each passageway (or the body region forming each passageway) to be adjusted so that the long axis of the passageway substantially matches the long axis of the nostril opening. Finally, an adjustable connector may allow the passageway (or the body region of the device forming each passageway) to be rotated, to better match the orientation of the nasal opening. Generally, human nasal openings are somewhat elliptical or tear-drop shaped. The body region forming the passageway, including a holdfast region, may be elliptically shaped, or otherwise shaped to match the shape of a nasal opening.

The movement or adjustability of the adjustable connector may be confined to these axes of motion. An adjustable connector may be adjustable only in a subset of these axes, such as rotation and nostril spacing. In some variations the adjustable connector includes compound motion. For example, both the nostril spacing and the nostril angular axis are adjusted simultaneously.

As used herein, an adjustable connector for a nasal device should be distinguished from a connector that is merely flexible. A flexible connector (such as those described in U.S. patent application Ser. No. 11/811,339, titled "Nasal Devices", herein incorporated by reference in its entirety) may be bent, stretched, or slightly compressed (typically within the elastic limit of the material forming the connector). However, a flexible connector generally has a single "set" configuration when force is not being applied to the connector; the spacing and orientation of the single-nostril devices connected by the connector are not fixed, but will tend to relax back to this "rest configuration." In contrast, an adjustable connector can be adjusted to multiple spacing and/or orientations of the single-nostril passageways of the device, and each position is effectively a rest position. After adjusting an adjustable connector, the new rest position will not relax back to the previous rest position. An adjustable connector may also be flexible, so that it is capable of flexing slightly (and returning to the current set position).

In some variations, the adjustable connector is lockable, so that once it is positioned, it may be substantially inhibited from additional adjustment of one or more of the adjustable axes (e.g., rotation, nostril spacing, nostril angle). For example, the adjustable connector may include a tensioning element that can be engaged to hold the position of the adjustable connector once it has been adjusted as desired. The lock may be repeatedly released (allowing further adjustment), or it may be single-use. For example, an adjustable connector may be one-time adjustable and "set" into a position, or the nasal device connector may be repeatedly adjustable.

A connector may include one or more adjustable joints, or points of adjustment, including ball joints, hinge joints, telescoping joints, rotating joints, and sliding joints. For example, a connector may include a ball joint that is linked to two arms; the ends of each arm may be attached (mounted) to the body regions of the whole-nose device forming the passageways. Examples of whole-nose nasal devices including adjustable connectors are described and illustrated below. In some variations, the adjustable connector is continuously adjustable. For example, the adjustable connector may include a ductile region (e.g., a wire) that can be bent anywhere along its length and be adjusted into shape without breaking. Some variations of adjustable connectors combine continuously adjustable regions with rigid or semi-rigid (e.g., flexible) regions. For example, an adjustable joint region may be formed from a continuously adjustable (e.g., ductile) material.

The adjustable joints or regions forming an adjustable connector may be relatively "stiff," meaning that they have some resistance to adjustment. The stiffness of an adjustable joint or region may be determined as the force required to displace the adjustable joint or region, and may be approximated over a range as a slope of force vs. displacement. An exemplary range for the stiffness may be between about 0.001 (or 0.01, or 0.1, or 1) N/mm to about 100 (or 0.1, or 1, or 5, or 10 or 50) N/mm. In some variations, the stiffness is variable. In some variations, the stiffness is adjustable. Thus, adjustable connectors that are lockable may be locked by increasing the stiffness of the adjustable region. In adjustable connectors having different adjustable joints or regions, the stiffness may be different for the different joints or regions. Devices having a moderate stiffness may be adjustable but maintain their set position (adjusted position) once adjusted.

EXAMPLES

Examples of whole-nose nasal devices are provided below. The examples provided herein are not intended to limit the invention to the embodiments shown, but are intended to illustrate various features or elements. Many of these features and elements may be combined or adapted for use within the same whole-nose nasal devices FIGS. 3A-3D show whole-nose nasal devices having a connector that is flexible. For example, FIG. 3A shows a whole-nose nasal device having a connector 301 that is semi-rigid. In this example the body regions 304, 304' forming the two passageways is integrally formed with the connector region 301. The connector region in this example is flexible, and may be formed of a polymeric material (e.g., a plastic or elastomeric material). Each passageway may include an airflow resistor (not visible in FIG. 3A).

The connector shown in FIG. 3A may be formed as an adjustable connector. For example, the connector may include a core wire (or ductile material) coated or surrounded by a protective layer (e.g., polymer), allowing the connector to be bent to reposition the passageways with respect to the nasal devices. Alternatively, an internal hinge region may also be included as part of the connector 301. In some variations, an additional holdfast may at least partially surround the regions of the device that are inserted into the subject's nostrils, in order to help secure the device in communication with each nostril. FIGS. 13A-13D, described in more detail below, illustrates one method of using a whole-nose nasal device such as that shown in FIG. 3A (particularly a whole-nose nasal device that includes an adjustable connector).

When the whole-nose nasal device shown in FIG. 3A is configured to include an adjustable connector 301 by including a hinge joint (or other adjustable joint) within the connector 301, the device may be adjustable in the nostril spacing axis. Thus, the two passageways of the whole-nose device may be separated from each other by opening or closing the adjustable joint. FIGS. 3B-3D illustrate other variations of whole-nose nasal devices that may be configured as adjustable connectors.

FIG. 3B is a whole-nose nasal device including a connector 311 that is configured as a bendable adjustable joint. The central region of the connector is hinged, as shown, and may include an internal wire (or other ductile material) or one or more internal hinge joints. Although the material forming the connector may be somewhat flexible or elastic, ideally the material is configured (e.g., by including an internal structure) so that it can hold the selected shape to which the connector is adjusted, without requiring additional force. The connector shown in FIG. 3B is adjustable in the nostril spacing axis. In addition, the connector is shown including a mount 316, 316' at either end of the connector. Each mount is configured to secure to the body region forming the passageways. As mentioned above, these body regions may themselves be "single-nostril" devices (referring to the subassembly of the passageway, body, airflow resistor and/or holdfast). The mount to which the body region attaches is configured as a rotating joint, as indicated by the arrow 319. This rotating joint allows the device to rotate along the axis indicated, permitting the body region (and any attached holdfast region) to be oriented with respect to the subject's nose.

FIG. 3C is another whole-nose nasal device that includes a connector 320 that is made of articulating segments 321, 322, 323, 324. In some variations the first 321 and last 324 segments are rigid, and are attached to more flexible (or continuously flexible) segments 322, 323 (or a single continuously flexible segment) allowing the device to be configured to the individual subject's anatomy. In some variations the segments 321, 322, 323, 324 forming the connector are all relatively rigid (or semi-rigid) and are connected by adjustable joints. For example, the segments (e.g., 322, 323) may be telescoping segments that slide over and within each other to change the length of the connector region 320, allowing the device to adjust in the nostril spacing axis. The connector may be mounted at their distal ends to the regions of the device forming the passageways by a fixed mount or an adjustable mount. If the mount is adjustable (e.g., by a hinge joint) the device may be adjustable in the nostril angle axis.

FIG. 3D shows another variation of a connector 331. In this example, the connector 331 a wire mounted to the single-nostril devices 334, 334' at either end. Thus, the device may be continuously flexible over the length of the wire, and can be adjusted over the entire length of the connector. Because the wire is relatively stiff, the connector may hold the position selected.

Other examples of continuously flexible connectors are shown in FIGS. 4A-4D. FIG. 4A shows a flexible connector 401 in an opened position. The connector includes openings at either end 402, 402' into which the structures forming the passageway and airflow resistor (not shown) are held. The ends of the connector are also configured as holdfast regions that may be inserted into the subject's nose and held therein. For example, the ends may be made in part of a compressible material (e.g., foam) that can be compressed for insertion, and expand to secure the device in each nostril. FIG. 4B illustrates the device of FIG. 4A in a bent configuration. FIGS. 4B and 4C similarly illustrate another variation of a whole-nose device including a connector. In this example, the connector 411 is made of a flexible polymeric material that (at both ends of the connector) partly surrounds two single-nostril nasal devices 415, 415', without blocking the passageways through them. The connector 411 at either end is doubled back on itself, forming a holdfast region 413 that can be inserted into the subject's nostrils. In some variations, the connector is made of a clear polymeric material.

The devices shown in FIGS. 4A-4D may also be configured as adjustable connectors by including a wire or other element within the length of the connector. In FIG. 4C, the transparent connector 411 includes a ductile wire filament 421. Including a ductile wire as part of the connector permits the connector to retain the set adjusted shape. Alternatively, the connector may be configured as an adjustable connector by including a joint (e.g., a hinge joint, a ball joint, etc.) within the connector. For example, the connector may comprise segments (e.g., stiff segments) connected by an adjustable joint and surrounded by a foam or other flexible material.

Figure 5A:
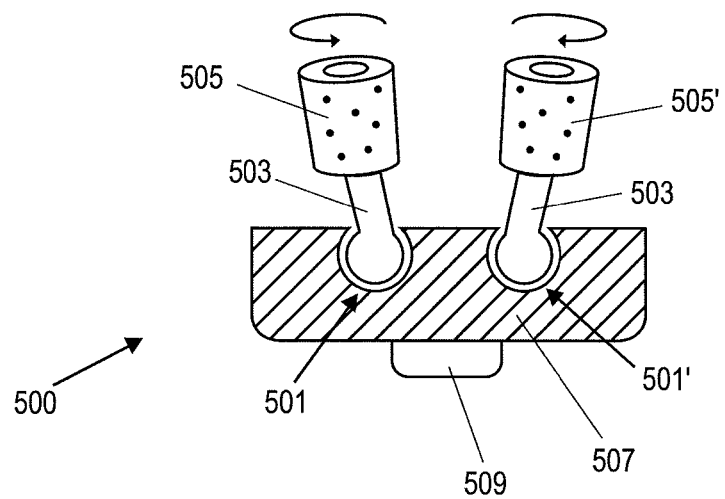
FIG. 5A is another variation of a whole-nose nasal device having a ball joint.

Adjustable connectors having one or more joints are shown in FIGS. 5A-10. For example, an adjustable connector 500 including two ball joints is shown in FIG. 5A. In this example, each of the single-nostril nasal devices 505, 505' are mounted to a stiff connector arm 503, 503', and the connector arms are each joined to a cross-bar 507 by a ball joint 501, 501'. The ball joints can be moved in the sockets formed in the cross-bar, allowing the rotational and angular adjustment of the single-nostril nasal devices (e.g., adjustment of the nostril angular axis and the angle). In some variations the cross-bar 507 is also extendable (e.g., by an additional telescoping joint).

The connector 500 in FIG. 5A is also lockable, and includes a lock and lock release 509, shown in this example as a button. Pushing the lock release button 509 may release a boss in the ball joint (e.g., by releasing a spring-loaded boss or other projection that compresses the ball socket), allowing the movement of the ball joint and adjustment of the relative positions of the single-nostril devices.

Figure 5B:
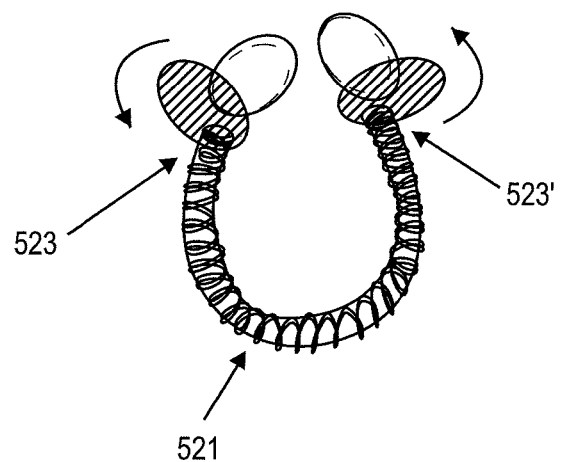
FIG. 5B is another variation of a whole-nose nasal device.

FIG. 5B is another variation of a whole-nose nasal device in which the single-nostril devices are mounted to the connector 521 at ball joints 523, 523'. In this variation, the connector 521 is configured as a flexible connector over its entire length, shown here as a spring. Thus, the ball joints 523, 523' allow the rotation and nostril angular axis of each single-nostril device to be adjusted independently.

Figure 6A:
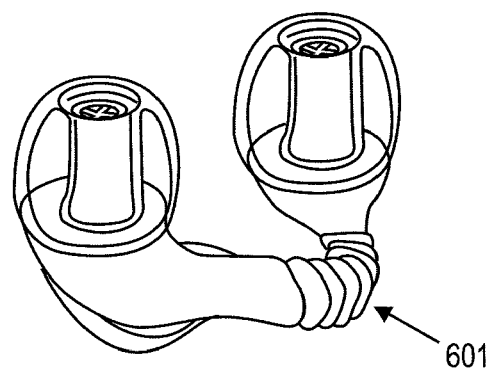
FIGS. 6A and 6B show a whole-nose nasal device having a hinge joint in a first and second configuration, respectively.
Figure 6B:
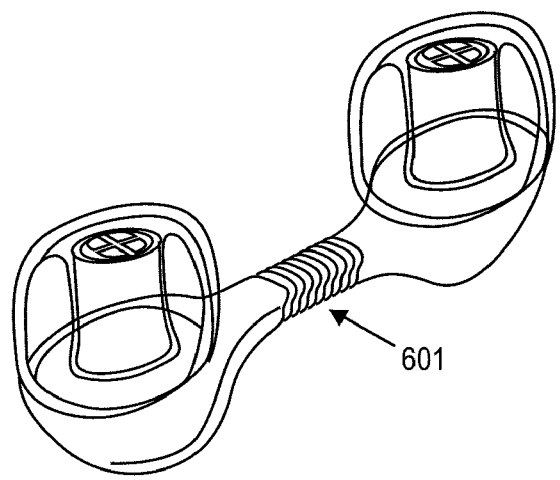

FIGS. 6A and 6B show another variation of a whole-nose device having an adjustable connector 601 that is a hinged joint. The adjustable connector shown in FIGS. 6A and 6B is generally rigid, but includes one (or more) adjustable joint regions, permitting bending and/or pivoting of the single-nostril nasal devices attached at either end. For example, the distance between each single-nostril nasal device or the angle between the devices may be adjusted. In the variations shown in FIGS. 6A and 6B, the joint region 601 comprises a bendable accordion region (similar to the bendable region of bendable straw).

Figure 6C:
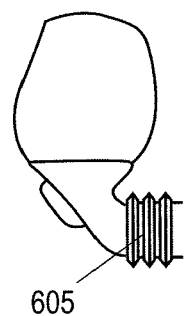
FIG. 6C shows one portion of a whole-nose nasal device.

The hinge joint in FIG. 6A is shown bent, decreasing the distance between the nasal device passageways that will be placed in communication with each nostril. In this example, bending the connector also modifies the rotation of the passageway relative to the nostril shape. In some variations the mount connecting each single-nostril nasal device (e.g., each passageway) to the connector may include a rotating joint (not shown), allowing independent adjustment of the rotation of each passageway. In addition, the end of the connector near each passageway may also (or alternatively) include an adjustable joint allowing adjustment of the nostril angular axis. FIG. 6C illustrates one variation of the end of a connector having an adjustable joint (hinge joint 605).

Figure 7:
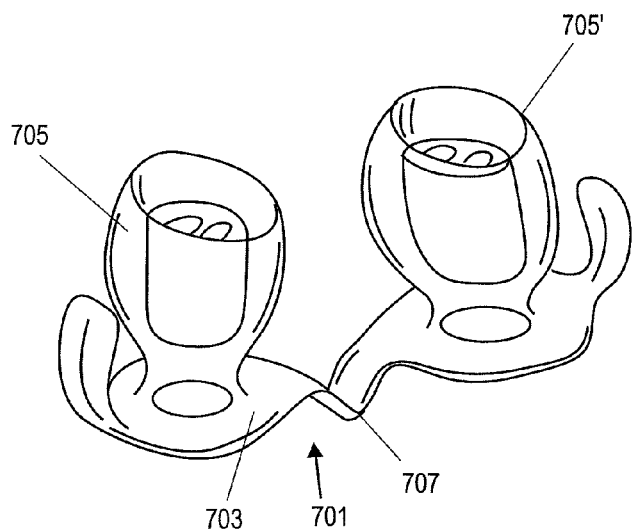
FIG. 7 is another variation of a whole-nose nasal device having a hinge joint.

FIG. 7 shows another variation of a hinge joint. In this example, the connector 701 is formed of a relatively stiff material that is bent to form a hinge joint 702 about which the ends of the connector may move towards or away from each other. In this example, the connector also includes a holdfast region, shown as a surface 703 surrounding each single-nostril device. The single-nostril devices also include individual holdfast regions (e.g., foam regions 705, 705') that may help secure the passageways in communication with each nostril. Although many of the whole-nose nasal devices described herein are configured so that the passageway regions are placed in fluid communication with the nostrils by inserting a holdfast region into each nostril, the connectors described herein may also be used as part of a whole-nose device configured to secure over or outside of each nostril.

Figure 8A:
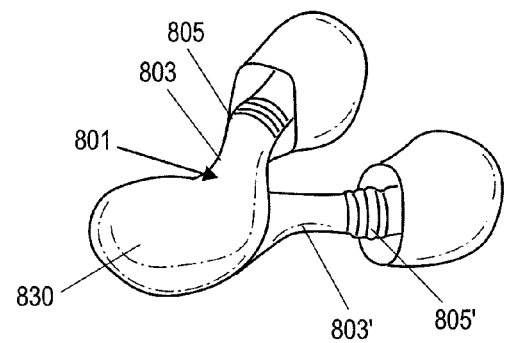
FIGS. 8A-8C show other variations of whole-nose nasal devices.
Figure 8B:
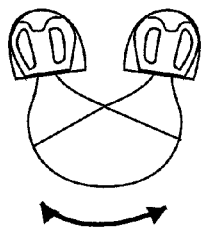
Figure 8C:
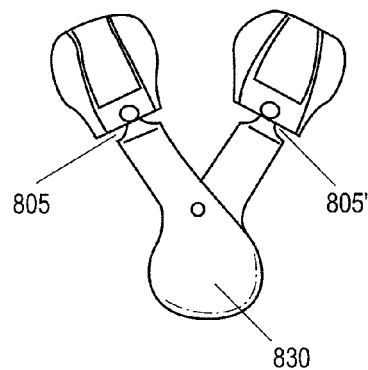

FIGS. 8A-8C show whole-nose devices having adjustable connectors that include hinge joints. For example, in FIG. 5A, the hinge joint 801 joins two relatively stiff arms 803, 803'. The stiff connector arms 803, 803' are each connected to a mount 805, 805' connecting them to each single-nostril device. As illustrated in FIG. 8C, the mounts in the connector 805 805' may be ball mounts, allowing the adjustment of the angle and rotation of the single-nostril devices. The nostril spacing can be adjusted by moving the connector arms 803, 803' relative to each other, as indicated by the arrow in FIG. 8B. The connector in FIGS. 8A-8C also includes a grip region 830 that can be held and manipulated by the user. Any of the connectors described herein may also be configured to include a handle or grip region.

Figure 9A:
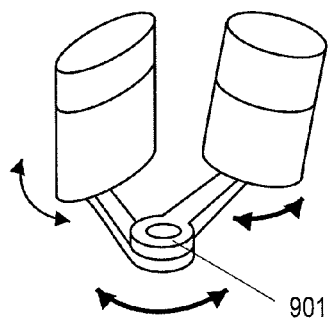
FIGS. 9A and 9B show variations of whole-nose nasal devices having hinge joints.
Figure 9B:
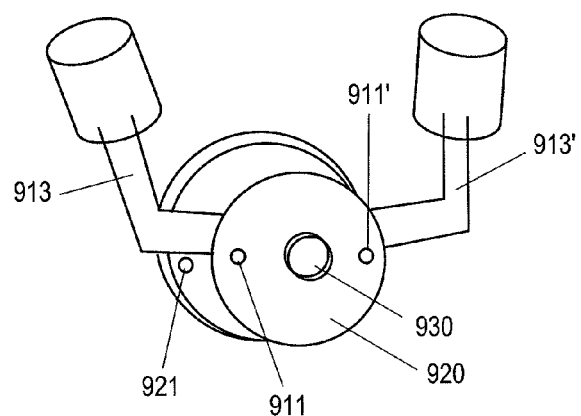

FIG. 9A is another example of a whole-nose device having a connector with a hinge joint. In this example the ends of the connector include rotating joints (not visible in FIG. 9), allowing the single-nostril devices to be rotated. Any of the hinge joints described herein may also include a lock to secure the position of the adjustable connector, as mentioned above. For example, FIG. 9B shows a device having two hinge joints 911, 911' to which two angled arms 913, 913' extend. A locking button 930 is included in the center of the hinge joint, which controls a lock that is configured to place tension on the arms 913, 913', securing them in place. For example, the connector may include friction plates 920, 921 that can be clamped together to lock the connector arms in position. The button 930 may be configured to either engage the lock or to disengage the lock. Although the examples shown here include an adjustable lock that is activated or inactivated by a button, any structure for activating and/or inactivating the joints may be used (e.g., a switch, screw, dial, clamp, etc.).

Figure 10:
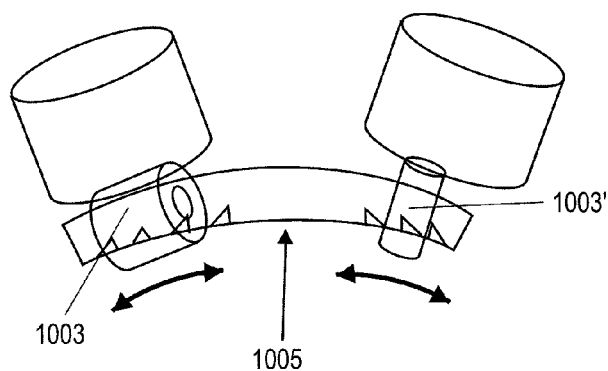
FIG. 10 is a whole-nose nasal device having a slide joint.

An adjustable connector may also include a sliding joint, as illustrated in FIG. 10. In this example, each single-nostril device is connected to an adjustable connector, including a connector arm (shown here as tubes 1003, 1003') that slides along a connector cross-piece 1005. The connectors may include mounts (including adjustable joints) for connecting to the single-nostril devices, allowing additional adjustability. The nostril spacing may be adjusted by sliding the connector arms 1003, 1003' along the connector cross-piece 1005. In this example the connector cross-piece includes retaining notches. In some variations, the retaining notches act as a zip-tie to hold the sliding joint in the selected position, or to prevent or limit movement in one direction. In some variations, the sliding joints include a lock release (or engagement) button or other control. The cross-piece 1005 in FIG. 10 may be flexible, rigid or semi-rigid.

The connectors described herein may be oriented in any appropriate manner. For example, the connectors shown in FIGS. 3A-10 span the region beneath the subject's nostrils, so that the connector extends beneath the nose when worn by a subject. In some variations, the connector is configured as an over-the-nose connector that extends over the top of the subject's nose when worn, as shown in FIGS. 11A-11F. In these variations, the connector may have an elongate frame (e.g., a wire frame or the like) that includes a single-nostril nasal device mounted at each end. The single-nostril nasal devices may seal within each nostril (as previously described), or an external (or combination internal/external) holdfast may be used. For example, an adhesive holdfast may be used. In some variations the over-the-nose connector may help hold the devices in place, preventing the single-nostril components from migrating to far into or out of the nasal passages. FIG. 11A is one example of an over-the-nose connector, and another example is shown in FIG. 11B. In FIG. 11A the over-the-nose connector is a flexible connector. In some variations the over-the-nose connector is an adjustable connector that includes one or more adjustable joints. Another variation of an over-the-nose connector is shown in FIG. 11C, and FIG. 11D illustrates the whole-nose device of FIG. 11C being worn by a subject. FIG. 11E is another schematic example of a whole-nose nasal device, which is shown on a nose in FIG. 11F.

The over-the-nose variations of the whole-nose nasal devices may also enhance the comfort of the device when worn by a subject. In some variations, the connector (top bridge) is custom fit to a subject. In some variations, the connector is reusable. The connector may also be rigid or semi-rigid (e.g., adjustable), and may include an outer padding (e.g., of foam) for comfort.

Figure 12A:
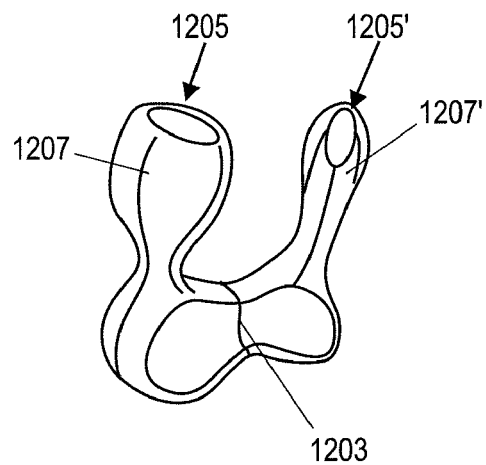
FIGS. 12A-12C are whole-nose nasal devices having a single airflow resistor.
Figure 12B:
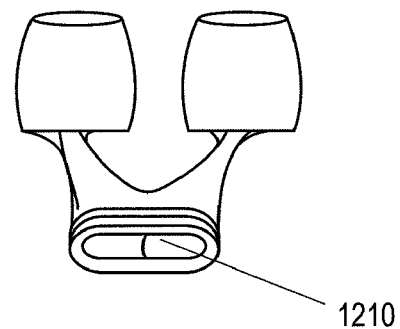
Figure 12C:
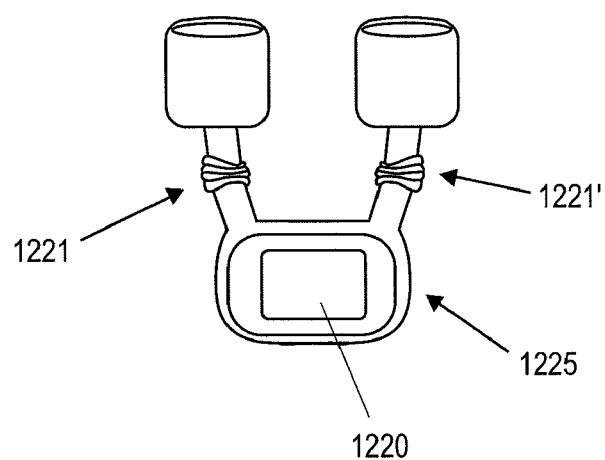

The majority of the whole-nose nasal devices described herein are configured so that each nostril is in communication with a single passageway and each passageway is in fluid communication with a separate airflow resistor. In some variations a single airflow resistor may be used for both nostrils. For example, FIGS. 12A-12C illustrate different variations of nasal devices including a single airflow resistor. These nasal devices typically include a single passageway that is configured to communicate with both of a subject's nostrils so that nasal respiration (but not oral respiration) occurs through the passageway. An airflow resistor (e.g., a flap valve) may be placed in communication with this single passageway, thereby regulating airflow through the nose. Any of the features previously described for single-nostril devices (e.g., devices in which each nostril is regulated by a separate airflow resistor) may be included as part of a whole-nose single airflow resistor device. For example, the whole-nose, single airflow-resistor device may include an adhesive holdfast that helps adhesively secure the device in communication with the subject's nose.

In FIG. 12A, each of two passages 1205, 1205' may be placed in fluid communication with s subject's nostril. The two passageways are formed with a body region that converges into a single passageway 1203, which is in communication with a single airflow resistor (not visible). In this example, each of the body regions 1207, 1207' surrounding the passages is in initial communication with the nostrils. FIG. 12B is another variation of a whole-nose device having a single airflow resistor 1210. FIG. 12C is another variation of a whole-nose device with a single airflow resistor that includes an adjustable connector 1225, having two adjustable joints 1221, 1221' as described above. The central passageway includes the airflow resistor (1220).

In operation, a whole-nose nasal device can be applied by first preparing the device to be worn. For example, the device may be removed from any packaging or any protective covering. A whole-nose nasal device may be packaged as a single piece, with the connector attached to each passageway or body region forming the passageway to communicate with the subject's nostrils. In some variations, particularly those having a reusable connector or other portion, the device may be assembled by the subject (e.g., by attaching the connector to two single-nose devices. Next, the whole-nose device can be adjusted by the subject (or a person applying the device to the subject) to fit their nose configuration. For example, in variations including an adjustable connector, the device may be bent or pushed into an insertion configuration approximating the spacing of the subject's nostrils. Thus, the adjustable connector may be adjusted to approximate the distance between the subject's nostrils, the angle of the nostrils and/or the rotation of the nostril openings, so that the portions of the whole-nose nasal device forming the passageways will match the openings. The device may then be applied to the subject and any additional adjustments made so that the device fits comfortably, and can be secured in communication with the subject's nostrils so that airflow through the nostrils passes through the device.

Figure 13D:
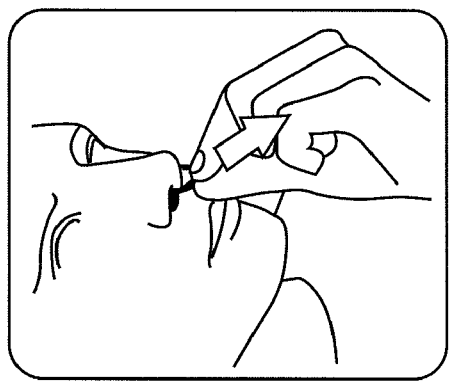
FIG. 13 illustrates the application of on variation of a whole-nose nasal device.
Figure 13C:
Figure 13B:
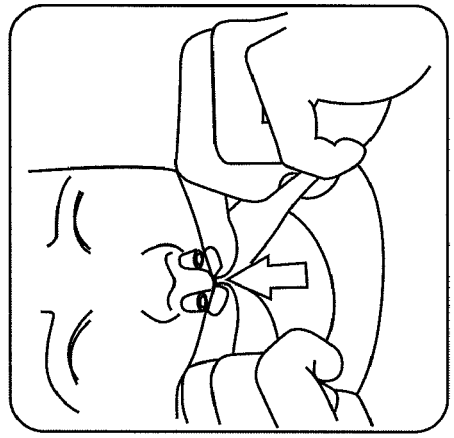
Figure 13A:
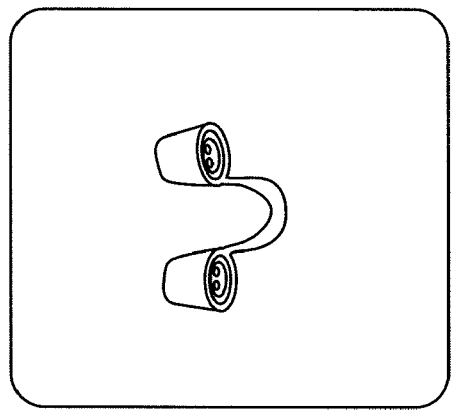

FIGS. 13A-13D illustrate one variation of a whole-nose nasal device having an adjustable connector. FIG. 13A shows the whole-nose nasal device including an adjustable connector; this nasal device may be adjusted by pushing or pulling on the connector, and/or by rotating the individual body regions forming the passageways (holding the airflow resistors). For example, the adjustable connector may include a bend region (e.g., a ductile wire surrounded by foam and/or polymer). In some variations, the adjustable connector includes a hinge joint near the center of the adjustable connector (in this figure, the hinge is surrounded by a foam or polymeric material, providing a protective layer that can protect the subject from pinching by the hinge); this hinge can be opened or closed to adjust the nasal device. After adjusting the whole-nose device, it may be initially inserted into the nose, as shown in FIG. 13B, and further adjusted so that it fits comfortably and snugly.

The whole-nose nasal device shown in FIGS. 13A-13D includes a holdfast region surrounding each of the passageways that are placed in communication with each nostril. In this variation, the whole-nose nasal device is inserted into the subject's nose, and the holdfast (e.g., a compressible foam) secures the device therein. This is shown in FIG. 13C. In some variations, the connector may also help hold the device in the subject's nose. For example, the adjustable connector may be adjusted so that the spacing between the passageways is slightly smaller than the spacing of the subject's nostrils, resulting in the device exerting a slight pressure on the septal region of the nose, helping to hold it is place (e.g., using an adjustable connector that is also flexible). In other variations, the holdfast region includes an adhesive holdfast that helps hold the device in position. The device may be further adjusted for comfort. After use, the device may be removed, as shown in FIG. 13D. In some variations, the adjustable connector may also help prevent the device from being inserted too far into the subject's nostril.

Whole-nose nasal devices may be customizable. For example, a whole nose nasal device may be set (or pre-set) to fit a specific subject. A connector may be customized to fit a particular subject, or sized to fit a specific class of subjects. For example, a size range of connectors may be prepared (e.g., small, medium, large, or based on numeric size ranges). A subject can be provided with a connector that is chosen based on the size measured from the subject's face. In some variations, the connector may be fabricated or adjusted specifically to fit the particular subject who will wear the nasal device.

Figure 14A:
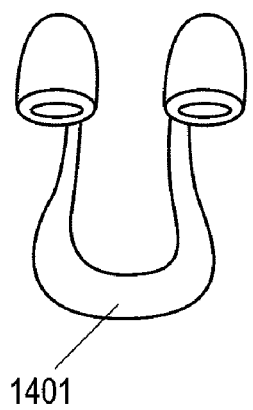
FIG. 14A is a customizable whole-nose nasal device and FIG. 14B illustrates activation of the device of FIG. 14A.
Figure 14B:
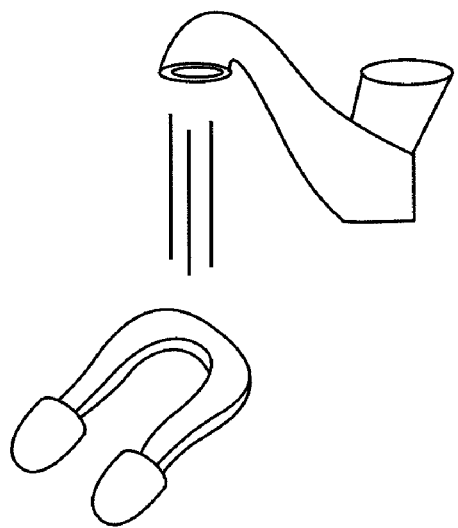

FIG. 14A show a patient-customizable nasal device that is configured to be set to conform to a patient's nose (e.g., nostril spacing). In FIG. 14A, the connector region 1401 of the device includes a water- or heat-activated material. Thus, the connector region of the nasal device is made pliable by wetting the device (e.g., with hot water, as illustrated in FIG. 14B) or by applying heat, and can be inserted into the nose comfortably. After cooling and/or drying, device retains this conformation. Thus, the device is custom-fit to the subject. The connector may be single-use (e.g., custom fit with each new device) or it may be re-used as part of a new nasal device by replacing the other components of the device such as the body regions containing the passageway and the airflow resistor(s).

Respiratory devices (including the connectors, holders, etc.) and inserters for respiratory devices may be made from any appropriate material or materials. In certain embodiments, the devices include a shape memory element or elements, for the passageway, and/or as part of the holdfast, connector, or airflow resistor. Any convenient shape memory material that provides for flexibility may be employed in these embodiments. For example, shape memory alloys may be used. A variety of shape memory alloys are known, including those described in U.S. Pat. Nos. 5,876,434; 5,797,920; 5,782,896; 5,763,979; 5,562,641; 5,459,544; 5,415,660; 5,092,781; 4,984,581; the disclosures of which are herein incorporated by reference in their entirety. The shape memory alloy that is employed should generally be a biocompatible alloy. Biocompatible alloys may include nickel-titanium (NiTi) shape memory alloys sold under the Nitinol™ name by Memory Corporation (Brookfield, Conn.). Also of interest are spring steel and shape memory polymeric or plastic materials, such as polypropylene, polyethylene, etc. In particular, the connectors described herein may be completely or partially made of a shape memory material.

Rubber and polymeric materials may also be used as part (or all) of the nasal devices described herein. Injection moldable materials such as polyether block amide (e.g., PEBAX®), and the like may be used. Materials which may be used include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins).

Biocompatible materials may be used, particularly for those portions of the device (e.g., the holdfast, connector, etc.) which may contact a user. In addition to some of the materials described above, the biocompatible materials may also include a biocompatible polymers and/or elastomers. Suitable biocompatible polymers may include materials such as: a homopolymer and copolymers of vinyl acetate (such as ethylene vinyl acetate copolymer and polyvinyl chloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art.

The devices described herein may be used to treat a disorder, particularly respiratory and/or sleeping disorders (including snoring and/or sleep apneas). For example, the devices described herein may be used to improving oxygen saturation, decreasing respiratory rate, and increasing tidal volume. The devices may also provide beneficial cardiac effects and may provide increased expiratory resistance during sleep or throughout the entire day.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Further, the drawings and illustrations provided herein may not be to scale; in particular, certain features may be exaggerated or minimized.

What is claimed is:

1. A nasal device adapted to be secured in communication with a subject's nasal passage, comprising:
a first passageway through a first body, wherein the first passageway is configured to fluidly connect with a subject's first nasal passage;
a second passageway through a second body, wherein the second passageway is configured to fluidly connect to a subject's second nasal passage;
a passive airflow resistor configured to be secured outside of the subject's nose and connect with both the first passageway and the second passageway, wherein the airflow resistor is configured to increase the resistance to exhalation through the nasal device more than inhalation through the nasal device to create expiratory positive airway pressure;
a holdfast configured to secure the nasal device in communication with the subject's nasal passages; and
a connector connecting the first body and the second body.

2. The device of claim 1, wherein the connector is a telescoping joint, a sliding joint, or a continuously flexible joint.

3. The device of claim 1, wherein the connector is selected from the group consisting of: a bendable wire, a spring, an accordion tube.

4. The device of claim 1, wherein the holdfast is part of the connector.

5. A whole-nose nasal device comprising:
a passageway configured to receive airflow from both of a subject's nasal passages so that nasal breathing, but not oral breathing, will occur through the passageway; and
a passive airflow resistor in a portion of the passageway located outside of the subject's nasal passages, wherein the airflow resistor is configured to inhibit expiration through the nasal device more than inspiration through the nasal device to create expiratory positive airway pressure.

6. The device of claim 5, further comprising a holdfast configured to at least partly secure the device to the subject's nose so that the passageway is in communication with both of the subject's nasal passages.

7. A method of treating a disorder using a nasal device, wherein the nasal device includes a first passageway configured to communicate with a subject's right nasal passage and a second passageway configured to communicate with the subject's left nasal passage, a passive airflow resistor located outside of the subject's nasal passages, wherein the passive airflow resistor receives airflow from both the first and second passageways and inhibits expiration through the nasal device more than it inhibits inhalation through the nasal device to create expiratory positive airway pressure, and a connector, wherein the method comprises:
applying the nasal device so that the first passageway is in communication with the subject's right nasal passage and the second passageway is in communication with the subject's left nasal passage while the passive airflow resistor is outside of the subject's nasal passages; and securing the nasal device to the subject.

8. The method of claim 7, wherein the disorder to be treated is selected from the list consisting of: respiratory disorders, sleep disorders, gastroenterologic disorders, and cardiovascular disorders.

9. A method of treating a disorder using a whole-nose nasal device, wherein the whole-nose nasal device includes a body having a first passageway and a second passageway; and a passive airflow resistor in fluid communication with the first and second passageways, wherein the airflow resistor is configured to inhibit expiration through the nasal device more than inspiration through the nasal device to create expiratory positive airway pressure, the method comprising:

securing the first passageway of the nasal device in communication with the subject's right nasal passage and the second passageway of the nasal device in communication with the subject's left nasal passage while the passive airflow resistor is outside of the subject's nasal passages; and inhibiting nasal expiration more than nasal inspiration.

* * * * *